(12) United States Patent
Fang et al.

(10) Patent No.: US 10,993,821 B2
(45) Date of Patent: May 4, 2021

(54) DOUBLE-LAYER BLOOD VESSEL STENT

(71) Applicant: LIFETECH SCIENTIFIC (SHENZHEN) CO., LTD, Shenzhen (CN)

(72) Inventors: Yi Fang, Shenzhen (CN); Benhao Xiao, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 0 days.

(21) Appl. No.: 16/957,883

(22) PCT Filed: Dec. 18, 2018

(86) PCT No.: PCT/CN2018/121732
§ 371 (c)(1),
(2) Date: Jun. 25, 2020

(87) PCT Pub. No.: WO2019/128775
PCT Pub. Date: Jul. 4, 2019

(65) Prior Publication Data
US 2020/0315822 A1 Oct. 8, 2020

(30) Foreign Application Priority Data
Dec. 29, 2017 (CN) .......................... 201711487996.3

(51) Int. Cl.
*A61F 2/852* (2013.01)
*A61F 2/07* (2013.01)

(52) U.S. Cl.
CPC ................ *A61F 2/852* (2013.01); *A61F 2/07* (2013.01); *A61F 2210/0076* (2013.01); *A61F 2250/0039* (2013.01); *A61F 2250/0098* (2013.01)

(58) Field of Classification Search
CPC .............. A61F 2002/0065; A61F 2/852; A61F 2002/823; A61F 2002/075;
(Continued)

(56) References Cited

U.S. PATENT DOCUMENTS

2006/0064156 A1  3/2006  Thistle et al.
2009/0259286 A1  10/2009  Ohri et al.
(Continued)

FOREIGN PATENT DOCUMENTS

CN  102697587 A  10/2012
CN  104382671 A  3/2015
(Continued)

OTHER PUBLICATIONS

International Search Report dated Mar. 15, 2019 in corresponding International application No. PCT/CN2018/121732; 4 pages.
(Continued)

*Primary Examiner* — Suba Ganesan
(74) *Attorney, Agent, or Firm* — Maier & Maier, PLLC (57) ABSTRACT

A double-layer blood vessel stent. A skirt-sided stent is provided on a main body stent. A first developing member and a second developing member are provided on the main body stent. The first developing member includes a first developing portion and a second developing portion, where the first developing portion and the second developing portion are flush with a free end at a position where the distance between the intersections on a plane perpendicular to the direction of an axis of the main body stent is the minimum distance; and an end, away from a first end, of the second developing member is flush with an end away from a tapered section of an extending section. This structure allows for accurate positioning of the double-layer vessel stent.

15 Claims, 3 Drawing Sheets

(58) Field of Classification Search
CPC ........ A61F 2002/077; A61F 2250/0096; A61F 2250/0097; A61F 2250/0098
See application file for complete search history.

(56) References Cited

U.S. PATENT DOCUMENTS

| | | | | |
|---|---|---|---|---|
| 2011/0319983 | A1* | 12/2011 | Zhu | A61F 2/07 623/1.35 |
| 2018/0185132 | A1* | 7/2018 | Baxter | A61F 2/06 |
| 2018/0333251 | A1* | 11/2018 | Zigelboim | A61F 2/962 |

FOREIGN PATENT DOCUMENTS

| | | |
|---|---|---|
| CN | 104758090 A | 7/2015 |
| CN | 104799974 A | 7/2015 |
| CN | 204709077 U | 10/2015 |
| CN | 204798068 U | 11/2015 |
| CN | 105496603 A | 4/2016 |
| CN | 105662511 A | 6/2016 |
| CN | 106580518 A | 4/2017 |
| CN | 107427377 A | 12/2017 |
| CN | 206714859 U | 12/2017 |
| WO | 2011/140973 A1 | 11/2011 |
| WO | 2017/005107 A1 | 1/2017 |

OTHER PUBLICATIONS

First Office Action dated Dec. 4, 2019 in corresponding Chinese application No. 201711487996.3; 9 pages.
Notification to Grant dated Dec. 31, 2019 in corresponding Chinese application No. 201711487996.3; 3 pages.

* cited by examiner

DOUBLE-LAYER BLOOD VESSEL STENT

FIELD

The embodiments relate to the field of medical apparatuses and instruments, in particular to a double-layer blood vessel stent.

BACKGROUND

At present, an endoluminal stent may be used for endovascular graft exclusion to isolate a lesion region within a lumen of a human body, for example, an endoluminal stent may be used to isolate arterial dissection or aneurysm in a blood vessel. Due to the advantages of low operation wound, small intraoperative blood transfusion volume, rapid postoperative recovery, short hospital stays and the like, such kind of method has gradually replaced the conventional lumen-opening surgery. Usually, the endoluminal stent has radial expansion capability and is fixed in lumen by its radial support force against the wall of vessel lumen. To avoid falling off, the stent needs to have enough radial support force, and the stronger the radial support force is, the stronger the rigidity of the stent after radial expansion is. However, due to individual differences, and different shapes of inner wall of lumens as well as changes in the features of the inner wall of lumen caused by a possibility of calcified plaque thereon, the endoluminal stent with stronger rigidity may cause poor adhesion between the stent and the lumen, resulting in the failure of complete closure between the stent and the inner wall of lesion lumen.

In order to solve the above-mentioned problems, one method is to use a double-layer blood vessel stent, namely, a skirt-sided stent with better deformability is arranged on an outer layer of a main body stent; but due to the complex structure of the double-layer stent, how to accurately release the double-layer blood vessel stent into a blood vessel becomes a problem to be solved urgently.

SUMMARY

Based on this, it is necessary to provide a double-layer blood vessel stent for facilitating accurate positioning in view of the above problem.

A double-layer blood vessel stent includes a main body stent, a skirt-sided stent and a developing member; the main body stent includes a first end and a second end arranged opposite to the first end.

The skirt-sided stent is arranged outside the main body stent and extends towards the first end; the skirt-sided stent includes a tapered section and an extending section, and the tapered section is provided with a connecting end and a free end opposite to the connecting end, and the connecting end is connected with the main body stent, and the free end is connected with the extending section; the developing member includes a first developing member and a second developing member; the first developing member is located between the first end and the connecting end, and the second developing member is located between the first developing member and the first end.

The first developing member includes a first developing portion and a second developing portion, the first developing portion extends along a first direction, the second developing portion extends along a second direction; the second direction obliquely intersects with the first direction, and the length of the first developing portion and the developing portion in an axial direction of the main body stent are both not less than 0.5 mm.

A distance between the intersections of the first developing portion and the second developing portion on a plane perpendicular to the axial direction of the main body stent gradually increases from a position where the distance between the intersections of the first developing portion and the second developing portion on a plane perpendicular to the axial direction of the main body stent is the minimum distance to an end, away from a connecting end, of the first developing portion or the second developing portion. The minimum distance between the intersections of the first developing portion and the second developing portion on a plane perpendicular to the axial direction of the main body stent is not greater than 2 mm.

The first developing portion and second developing portion are flush with one end of the free end at a position where a distance between the intersections of the first developing portion and the second developing portion on a plane perpendicular to an axial direction of the main body stent is minimum; and one end, away from a first end, of the second developing portion is flush with one end, away from a tapered section, of the extending section.

In one of the embodiments, a distance between the intersections of one end, close to the connecting section, of the first developing portion and one end, close to the connecting section, of second developing portion, on the plane perpendicular to the axial direction of the main body stent is the minimum distance.

In one of the embodiments, the second developing member includes a third developing portion and a fourth developing portion, the third developing portion extends along a third direction, and the fourth developing portion extends along a fourth direction, the fourth direction obliquely intersects with the third direction, moreover, and length of the third developing portion and the fourth developing portion in the axial direction of the main body stent is not less than 0.5 mm.

A distance between the intersections of the third developing portion and the fourth developing portion on a plane perpendicular to the axial direction of the main body stent gradually increases from a position where the distance between the intersections of the third developing portion and the fourth developing portion on a plane perpendicular to the axial direction of the main body stent is the minimum distance to an end, away from the connecting end, of the third developing portion or the fourth developing portion. The minimum distance between the intersections of the third developing portion and the fourth developing portion on a plane perpendicular to the axial direction of the main body stent is not greater than 2 mm.

A distance between the intersections of one end, away from the first end, of the third developing portion and one end, away from the first end, of the fourth developing portion, on the plane perpendicular to the axial direction of the main body stent is the minimum distance.

In one of the embodiments, the main body stent includes a first bare stent and a main body coating film attached on the first bare stent; the first developing portion, the second developing portion, the third developing portion, and the fourth developing portion are all disposed on the first bare stent.

In one of the embodiments, the first bare stent includes a plurality of axially arranged wave rings, and the wave ring include a plurality of alternately arranged wave crests and wave troughs, and the adjacent wave crest and wave trough are connected with each other via wave rod; the first developing portion and the second developing portion are located on two adjacent wave rods of one of the wave rings, and the third developing portion and the fourth developing portion are located on two adjacent wave rods of another wave ring.

In one of the embodiments, the lengths of the first developing portion, second developing portion, third developing portion and the fourth developing portion are all ½ to ⅔ of that of the corresponding wave rods.

In one of the embodiments, an included angle from the position where a distance between the intersections of the first and second developing portions on a plane perpendicular to an axial direction of the main body stent is the minimum distance, to the position where the distance between the intersections of the third and fourth developing portions on a plane perpendicular to an axial direction of the main body stent is the minimum distance, covered in a peripheral direction of the main body stent is not greater than 15°.

In one of the embodiments, an axial distance from the position where the distance between the intersections of the first and second developing portions on a plane perpendicular to an axial direction of the main body stent is the minimum distance, to an end, away from the first end, of the second developing member ranges from 10 mm to 15 mm.

In one of the embodiments, an axial distance from an end, away from the first end, of the second developing member to the first end ranges from 10 mm to 15 mm.

In one the embodiments, a distance from each position on the extending section to the longitudinal center axis of the main body stent is equal.

In one of the embodiments, the sum of the length of the contour line of the tapered section and the length of the contour line of the extending section is not greater than an axial distance between the connecting end and the first end of the main body stent.

In one of the embodiments, the developing member further includes a third developing member and a fourth developing member, and the third developing member is arranged on the first end, and the fourth developing member is arranged on the second end.

A specific first developing member is arranged between the first end and the second end of the above double-layer blood vessel stent, so as to conveniently observe the middle condition of the double-layer blood vessel stent, and the first developing member may be used to identify the distortion and folding of the double-layer blood vessel stent during its release process. Furthermore, the gradual developing member facilitates the observation of the release position of a skirt-sided stent in a sheathing canal, thereby ensuring the full release of the extending section of the skirt-sided stent, which is helpful to the accurate positioning of the double-layer blood vessel stent subsequently. In addition, a second developing member is arranged at a specific position, so as to achieve the accurate positioning of the double-layer blood vessel stent.

DETAILED DESCRIPTION OF EMBODIMENTS

To make the above objectives, features and advantages more apparent, detailed embodiments will be described in detail with reference to the accompanying drawings hereafter. In the following description, numerous specific details are set forth to make full sense of the embodiments. The embodiments may be implemented in many other different modes, and those of ordinary skill in the art may make similar improvements within the spirit and scope of the disclosure, therefore, the disclosure is beyond the detailed embodiments disclosed hereafter.

It can be noted that when a member is referred to as being "fixed" to another member, it may be directly fixed on another member or an intervening member may be present. When a member is referred to as being "connected" to another member, it may be directly connected to another member or intervening members may be present. The terms used in the article, e.g., "vertical", "horizontal", "left", "right" serve for illustrative purposes only, but are not intended to be the only embodiment.

Unless defined otherwise, all technical and scientific terms used herein have the same meaning as commonly understood by one of ordinary skill in the art. The terms used herein in the description are for the purpose of describing particular embodiments only and not intended to be limiting. The various technical features of the above-mentioned embodiments may be combined in any way, and in order to simplify the description, not all possible combinations of the features of the above-mentioned embodiments are described. However, as long as there is no conflict between these features, they should be considered to be within the scope of the disclosure.

Figure 1:
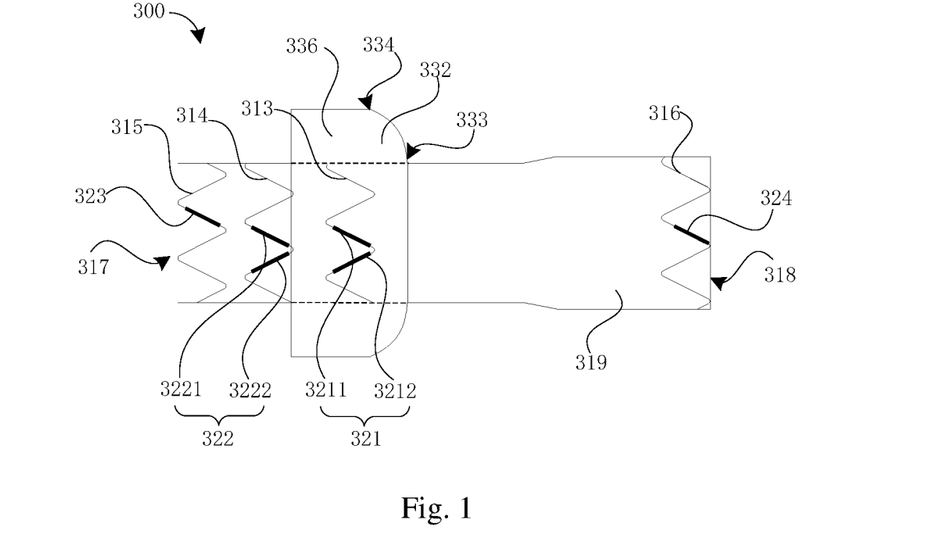
FIG. 1 is a schematic diagram showing a structure of a double-layer blood vessel stent in natural state in one embodiment.
Figure 2:
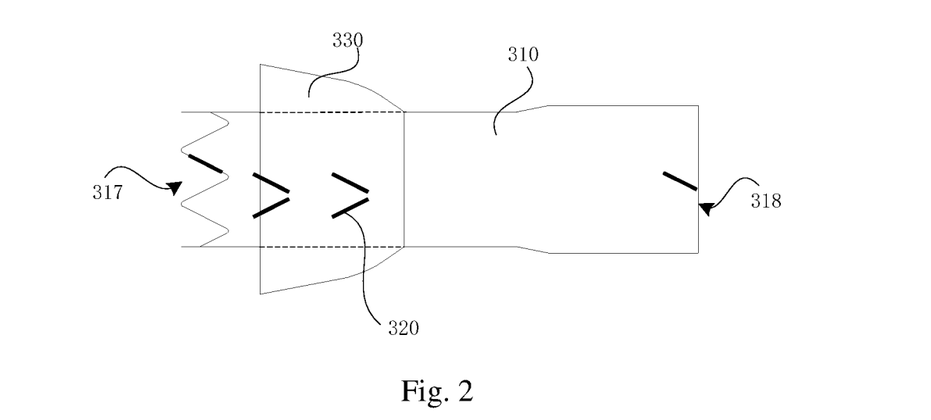
FIG. 2 is a schematic diagram showing a structure of a skirt-sided stent of the double-layer blood vessel stent as shown in FIG. 1 during sheathing process.

Referring to FIGS. 1 and 2, a double-layer blood vessel stent 300 of one embodiment includes a main body stent 310, a skirt-sided stent 330, and a developing member 320. The skirt-sided stent 330 is sleeved on the main body stent 310. The developing member 320 is disposed on the main body stent 310, and the main body stent 310 is provided with a first end 317 and a second end 318 disposed opposite to the first end 317. It can be understood that the first end 317 may be a proximal end of the main body stent 310, and the second end 318 may be a distal end of the main body stent 310.

Further, the main body stent 310 includes a first bare stent and a main body coating film 319. The main body coating film 319 is attached on the first bare stent. The main body stent includes a plurality of axially distributed wave rings. The wave rings includes a first wave ring 313, a second wave ring 314, a third wave ring 315, and a fourth wave ring 316. Further, the third wave ring 315 is arranged on the first end 317, the fourth wave ring 316 is arranged on the second end 318, and the first wave ring 313 is arranged between the third wave ring 315 and the fourth wave ring 316, and the second wave ring 314 is arranged between the first wave ring 313 and the third wave ring 315.

For example, the wave ring includes a plurality of alternately arranged wave crests and wave troughs, and adjacent wave crest and wave trough are connected through a wave rod. Further, an included angle formed by extension lines of two adjacent wave rods ranges within 30°-120°.

Figure 3:
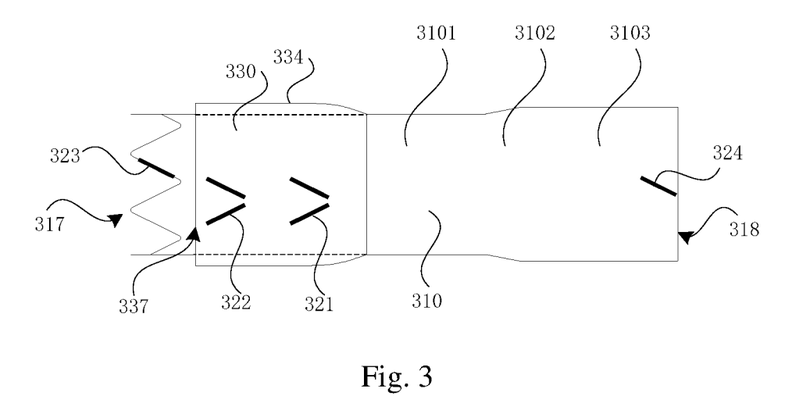
FIG. 3 is a schematic diagram showing a structure of the skirt-sided stent of the double-layer blood vessel stent as shown in FIG. 1 at an end of sheathing.

Referring to FIG. 3, the main body stent 310 is formed with a proximal portion 3101, a connecting portion 3102, and a distal portion 3103 that are sequentially connected. A first end 317 is formed on an end, away from the connecting portion 3102, of the proximal end 3101, and a second end 318 is formed on an end, away from the connecting portion 3102, of the distal portion 3103. The coating film of the first end 317 forms a petal-shaped structure, so that blood passes through the first end conveniently; the coating film of the second end 318 is a flush structure.

In one of the embodiments, cross-sectional area of proximal portion 3101 is smaller than that of the distal portion 3103. The cross-sectional area of one end, close to the proximal portion 3101, of the connecting portion 3102 is smaller than or equal to that of one end, close to the distal portion 3103, of the connecting portion 3102; and an included angle which is ranged within 0°-30° forms between an axial direction and a connecting line between the end, close to the proximal portion 3101, of the connecting portion 3102 and the end, close to the distal portion 3103, of the connecting portion 3102. Further, an included angle which is ranged within 15°-25° forms between the axial direction and a connecting line between the end, close to the proximal portion 3101, of the connecting portion 3102 and the end, close to the distal portion 3103, of the connecting portion 3102. The above structure enables the main body stent 310 to form a tapered structure, which may enhance the anchoring force of the distal portion 3103, and meanwhile inhibit the transmission of aorta pulsation to the distal portion 3103 of a branch vessel stent.

The skirt-sided stent 330 is sleeved outside the main body stent 310 and extends toward the first end 317. The skirt-sided stent 330 includes a tapered section 332 and an extending section 336 connected together. The tapered section 332 has a connecting end 333 and a free end 334 opposite to the connecting end 333. The connecting end 333 of the tapered section 332 is connected with the main body stent 310, and the free end 334 is connected with the extending section 336. Further, the distances from each position of the extending section 336 to a longitudinal center axis of the main body stent 310 are equal, that is, the extending section 336 is disposed in parallel with the main body stent 310. Further, the sum of a length of the contour line of the tapered section 332 and a length of the contour line of the extending section 336 are not greater than a distance between the connecting section 333 and the first end 317 of the main body stent 310 along the axial direction, so it can be avoided that the skirt-sided stent 330 exceeds the main body stent during sheathing, thus lowering sheathing length and decreasing the release stroke, as well as being beneficial to the unfolding state of the skirt-sided stent 330 after opening from the sheathing canal. It can be noted that the contour line of the tapered section 332 may be construed as the length of a curve between the connecting end 333 and the free end 334 intercepted when a plane passing through the axis of the main body stent 310 intersects with the tapered section 332. The contour line of the extending section 336 may be construed as the length of a curve between one end, away from the free end 334, of the extending section 336 and a free end intercepted when a plane passing through the axis of the main body stent 310 intersects with the extending section 336. In embodiments of the drawings, the contour line of the tapered section 332 is a curve.

In this embodiment, the skirt-sided stent 330 includes a second bare stent (not shown in the drawings) and a skirt-sided coating film (not shown in the drawings) attached on the second bare stent. The radial deformability of the skirt-sided stent 330 is better than the radial deformability of the main body stent 310.

Referring to FIGS. 1 and 2 as well, a developing member 320 is disposed on the main body stent 310. For example, the developing member 320 includes a first developing member 321, a second developing member 322, a third developing member 323, and a fourth developing member 324. The first developing member 321 is located between the first end 317 and the connecting end 333, and the second developing member 322 is located between the first developing member 321 and the first end 317. The third developing member 323 is arranged on the first end 317, and the fourth developing member 324 is arranged on the second end 318. The third developing member 323 serves to characterize an initial end of the double-layer blood vessel stent 300. The fourth developing member 324 serves to characterize a terminating end of the double-layer blood vessel stent 300.

Further, the first developing member 321 includes a first developing portion 3211 and a second developing portion 3212; the first developing portion 3211 extends in a first direction, and one end of the first developing portion 3211 is close to the first end 317, and another end is away from the first end 317; the second developing portion 3212 extends in a second direction, and the first direction obliquely intersects with the second direction; one end of the second developing portion 3212 is close to the first end 317, and another end of the second developing portion 3212 is away from the first end 317. For example, the length of the first developing portion 3211 and the length of the second developing portion 3212 on the axial direction of the main body stent are both not less than 0.5 mm. A distance between the intersections of the first developing portion 3211 and the second developing portion 3212 on a plane perpendicular to the axial direction of the main body stent 310 gradually increases from a position where the distance between the intersections of the first developing portion 3211 and the second developing portion 3212 on a plane perpendicular to the axial direction of the main body stent 310 is the minimum distance to an end, away from the connecting end 333, of the first developing portion 3211 or the second developing portion 3212. The minimum distance between the intersections of the first developing portion 3211 and the second developing portion 3212 on a plane perpendicular to the axial direction of the main body stent 310 is not greater than 2 mm. The first developing portion 3211 and the second developing portion 3212 are flush with the free end at a position where the distance between the intersections of the first developing portion 3211 and the second developing portion 3212 on the plane perpendicular to the axial direction of the main body stent 310 is the minimum distance. During operation, it may prevent the first developing member 321 from being blocked by developing rings in a sheathing canal when the first developing portion 3211 and the second developing portion 3212 gradually release from the sheathing canal; by gradually release of the first developing portion 321, it is beneficial to observe the release position of the skirt-sided stent 330 in the sheathing canal, thus guaranteeing the full release of the extending section 336 of the skirt-sided stent 330, and facilitating the accurate positioning of the double-layer blood vessel stent 300 subsequently.

In the present embodiment, a distance between the intersections of one end, close to the connecting end 333, of the first developing portion 3211, and one end, close to the connecting end 333, of the second developing portion 3212 on a plane perpendicular to the axial direction of the main body stent 310 is the minimum distance; the first developing portion 3211 and the second developing portion 3212 are symmetrical with each other on the axis of the main body stent 310. Further, in other embodiments, the position where a distance between the intersections of one end, close to the connecting end 333, of the first developing portion 3211 and one end, close to the connecting end 333, of the second developing portion 3212 on the plane perpendicular to the axial direction of the main body stent 310 is the minimum distance may be also located at the middle portion of the first developing portion 3211 and/or the second developing portion 3212.

Referring to FIG. 1, one end, away from the first end, of the second developing member 322 is in parallel to one end, away from the tapered section 332, of the extending section 336, which may facilitate the accurate positioning of the double-layer blood vessel stent 300. In the embodiments, the second developing member 322 includes a third developing portion 3221 and a fourth developing portion 3222; the third developing portion 3221 extends in a third direction, and one end of the third developing portion 3221 is close to the first end 317, and another end is away from the first end 317; the fourth developing portion 3222 extends in a fourth direction, and the third direction obliquely intersects with the fourth direction; one end of the fourth developing portion 3222 is close to the first end 317, and another end is away from the first end 317. The length of the third developing portion 3221 and the length of the fourth developing portion 3222 on the axial direction of the main body stent are both not less than 0.5 mm. A distance between the intersections of the third developing portion 3221 and the fourth developing portion 3222 on a plane perpendicular to the axial direction of the main body stent 310 gradually increases from a position where the distance between the intersections of the third developing portion 3221 and the fourth developing portion 3222 on a plane perpendicular to the axial direction of the main body stent 310 is the minimum distance to an end, away from the connecting end 333, of the third developing portion 3221 or the fourth developing portion 3222. The minimum distance between the intersections of the third developing portion 3221 and the fourth developing portion 3222 on a plane perpendicular to the axial direction of the main body stent 310 is not greater than 2 mm. A distance between the intersections of one end, close to the connecting end 333, of the third developing portion 3221 and one end, close to the connecting end 333, of the fourth developing portion 3222 on a plane perpendicular to an axial direction of the main body stent 310 is the minimum distance. For example, the third developing portion 3221 and the fourth developing portion 3222 are symmetrical with each other on the axis of main body stent 310.

It can be understood that in other embodiments, the second developing member 322 may be any other shape as long as one end, away from the first end 317, of the second developing member 322 is flush with one end, away from the tapered section 332, of the extending section 336.

Further, an included angle from the position where the distance between the intersections of the first developing portion 3211 and the second developing portion 3212 on a plane perpendicular to an axial direction of the main body stent 310 is the minimum distance, to the position where a distance between the intersections of the third developing portion 3221 and the fourth developing portion 3222 on a plane perpendicular to an axial direction of the main body stent 310 is the minimum distance, covered in a peripheral direction of the main body stent 310 is not greater than 15°, so that the distance between the developing member 321 and the second developing member 322 in a circumferential direction is smaller, thus checking whether the main body stent 310 shortens. For example, a connecting line between the position where a distance between the intersections of the first developing portion 3211 and the second developing portion 3212 on a plane perpendicular to an axial direction of the main body stent 310 is the minimum distance, and the position where a distance between the intersections of the third developing portion 3221 and the fourth developing portion 3222 on a plane perpendicular to an axial direction of the main body stent 310 is the minimum distance, is in parallel to the axis of the main body stent 310.

In the present embodiment, the first developing member 321 is arranged on the first wave ring 313. Further, the first developing portion 3211 and the second developing portion 3212 are respectively formed by coating, laminating, or winding developing materials on wave rods of the first wave ring 313. Further, the first developing portion 3211 and the second developing portion 3212 are located on two adjacent wave rods, and the first developing portion 3211 and the second developing portion 3212 are spaced to form a "V"-shaped structure. At this time, a distance between one end, where the first developing portion 3211 and the second developing portion 3212 are close to each other, of the first developing portion 3211 and one end, where the first developing portion 3211 and the second developing portion 3212 are close to each other, of the second developing portion 3212, is not greater than 2 mm. It can be understood that in other embodiments, the first developing portion 3211 is connected with one end of the second developing portion 3212 to form a "V"-shaped structure. For example, the length of the first developing portion 3211 and the length of the second developing portion 3212 respectively ranges from 2 mm to 4 mm; the length of the first developing portion 3211 is ½ to ⅔ of the length of the corresponding wave rod, and the length of the second developing portion 3212 is ½ to ⅔ of the length of the corresponding wave rod.

The second developing member 322 is arranged on the second wave ring 314. Further, the third developing portion 3221 and the fourth developing portion 3222 are respectively formed by coating, laminating, or winding developing materials on wave rods of the second wave ring 314. Further, the third developing portion 3221 and the fourth developing portion 3222 are located on two adjacent wave rods, and the third developing portion 3211 and the fourth developing portion 3212 are spaced to form a "V"-shaped structure. At this time, a distance between one end where the first developing portion 3211 and the second developing portion 3212 are close to each other, of the first developing portion 3211 and one end, where the first developing portion 3211 and the second developing portion 3212 are close to each other, of the second developing portion 3212, is not greater than 2 mm. It can be understood that in other embodiments, the third developing portion 3221 is connected with one end of the fourth developing portion 3222 to form a V-shaped structure. For example, the length of the third developing portion 3221 and the length of the fourth developing portion 3222 respectively ranges from 2 mm to 4 mm; the length of the third developing portion 3221 is ½ to ⅔ of the length of the corresponding wave rod, and the length of the fourth developing portion 3222 is ½ to ⅔ of the length of the corresponding wave rod.

The third developing member 323 is arranged on the third wave ring 315. Further, the third developing member 323 is formed by coating, laminating, or winding developing materials on wave rods of the third wave ring 315. For example, the third developing member 323 is "I"-shaped. Further, the length of the third developing member 323 ranges from 2 mm to 4 mm; the third developing member 323 is ½ to ⅔ of the length of the corresponding wave rod.

The fourth developing member 324 is arranged on the fourth wave ring 316. Further, the fourth developing member 324 is formed by coating, laminating, or winding developing materials on wave rods of the fourth wave ring 316. For example, the fourth developing member 324 is "I"-shaped. Further, the length of the fourth developing member 324 ranges from 2 mm to 4 mm; the fourth developing member 324 is ½ to ⅔ of the length of the corresponding wave rod.

It can be understood that in other embodiments, the developing member 320 may also be formed on the main body coating film 319. It can also be understood that the first developing member 321 may also be located on the skirt-sided stent 330.

Further, a distance between one end, away from the first end 317, of the second developing portion 322 and the first end 317 ranges from 10 mm to 15 mm, so that one end, away from the first end 317, of the second developing portion 322 is flush with an end portion of the main blood vessel stent when releasing. The above configuration may be easy to control the length of one end of the double-layer blood vessel stent beyond the main blood vessel stent from 10 mm to 15 mm, thus reducing the risk of the double-layer blood vessel stent's falling off from the main blood vessel stent.

Further, an axial distance from the position where a distance between the intersections of the first developing portion 3211 and the second developing portion 3212 on a plane perpendicular to an axial direction of the main body stent 310 is the minimum distance to one end, away from the first end 317, of the second developing member 322, ranges from 10 mm to 15 mm.

Referring to FIG. 1 again, a double-layer developing stent 300 is in a free state, and the tapered section 332 bends and extends towards a free end 334 from the connecting end 333. Further, a distance between one end, close to the first end 317, of the first developing member 321 and the connecting end 333 is equal to the length of the contour line of the tapered section 332. One end, away from the tapered section 332, of the extending section 336 is flush with one end, close to the connecting end 333, of the second developing member 321.

Referring to FIGS. 2 and 3 together, the free end 334 of the tapered section 332 is movable into abutment against the main body stent 310 towards a direction adjacent to the first developing member 321. FIG. 2 shows an intermediate state that the free end 334 moves against the first end 317, and FIG. 3 shows a state that the skirt-sided stent 330 is abutted against the main body stent 310. The free end 334 is flush with one end, away from the connecting end 333, of the first developing member 321, when the free end 334 is abutted against the main body stent 310.

Referring to FIGS. 1-3 together, when the double-layer blood vessel stent 300 in the above natural state is sheathing, the second end 318 of the stent 310 first enters the sheathing canal till the connecting end 333 enters the sheathing canal, and then, pushed by the inner wall of the sheathing canal, the tapered section 332 makes the free end 334 moving towards a direction close to the first end 317 until abutting against the main body stent 310. At this time, the tapered section 332 is in a snugged state and the free end 334 is flush with one end, away from the connecting end 333, of the first developing member 321, thus achieving the state as shown in FIG. 3 and completing the sheathing process of the double-layer blood vessel stent 300.

Figure 4:
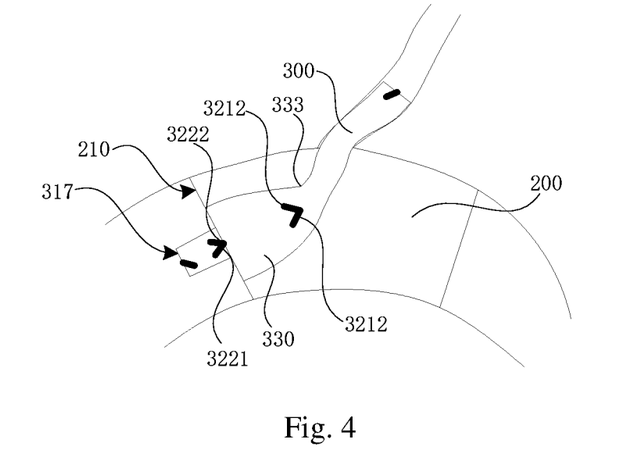
FIG. 4 is a schematic diagram showing a structure of the double-layer blood vessel stent as shown in FIG. 1 of one embodiment during branch vessel reconstruction.

Referring to FIG. 4, when the above double-layer blood vessel stent 300 is applied to a chimney technique as a chimney stent for vascular reconstruction, firstly, a conveyor equipped with a main blood vessel stent 200 is implanted in a main vessel, and a conveyor equipped with a double-layer blood vessel stent 300 is fed from a branch vessel. Moreover, proximal ends of the two conveyors are intersected, and then the main blood vessel stent 200 is released; the first end 317 is a forward end of the double-layer blood vessel stent 300 for moving while being implanted. Then, the double-layer blood vessel stent 300 is released until the first developing portion 3211 and the second developing portion 3212 thereof are just released from the conveyor at the position where a distance between the intersections of the first developing portion 3211 and the second developing portion 3212 on the plane perpendicular to the axial direction of the main body stent 310 is the minimum distance, stopping releasing at this time; the position of the double-layer blood vessel stent 300 is adjusted to complete the initial positioning of the implantation when the first developing portion 3211 and the second developing portion 3212 thereof are flush with the proximal end 210 of the main blood vessel stent 200 at the position where the distance between the intersections thereof on the plane perpendicular to the axial direction of the main body stent 310, which may ensure the expansion of the extending section 336 and shorten the stroke of the double-layer blood vessel stent dragged from the position to the final position. After that, a releasing device of the sheathing canal is locked, then the sheathing canal and the double-layer blood vessel stent 300 are dragged to move towards the branch vessel in the main blood vessel stent 200 until the third developing portion 3221 and the fourth developing portion 3222 are flush with the proximal end 210 of main blood vessel stent 200 at the position where a distance between the intersections of the third developing portion 3221 and the fourth developing portion 3222 on a plane perpendicular to the axial direction of the main body stent 310 is the minimum distance, stopping dragging at this time; the double-layer blood vessel stent 300 is completely released from the sheathing canal, and at this time, one end, away from the connecting end 333, of the skirt-sided stent 330 is flush with the proximal end 210 of the main blood vessel stent 200, thus achieving the reconstruction of branch blood flow.

Figure 5:
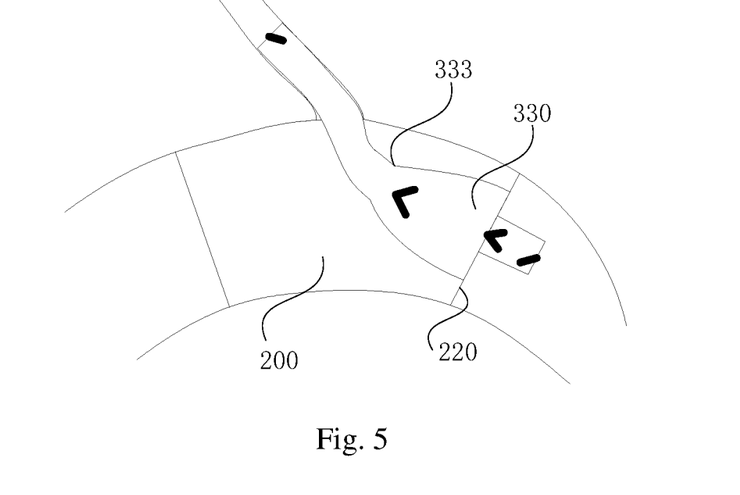
FIG. 5 is a schematic diagram showing a structure of a double-layer blood vessel stent as shown in FIG. 1 of another embodiment during branch vessel reconstruction.

FIG. 5 shows that the above-mentioned double-layer blood vessel stent 300 is applied for reconstruction of blood vessel so that one end, away from the connecting end 333, of the skirt-sided stent 330 is flush with the distal end 220 of the main blood vessel stent 200, thus achieving the reconstruction of branch vessel. The implementation is similar to that of FIG. 4 and will not be described in detail here thereby.

A specific first developing member 321 is arranged between the first end 317 and the second end 318 of the above double-layer blood vessel stent 300, which is convenient to observing the condition of the middle portion of the double-layer blood vessel stent 300, and may be used for identifying the distortion and folding of the double-layer blood vessel stent 300 during release process; moreover, by gradually changing of the first developing portion 321, it is beneficial to observe the release position of the skirt-sided stent 330 in the sheathing canal, thus guaranteeing the full release of the extending section 336 of the skirt-sided stent 330, and facilitating the accurate positioning of the double-layer blood vessel stent 300 subsequently. Moreover, the second developing member 322 is arranged at a specific position, which facilitates the accurate positioning of the double-layer blood vessel stent 300.

Figure 6:
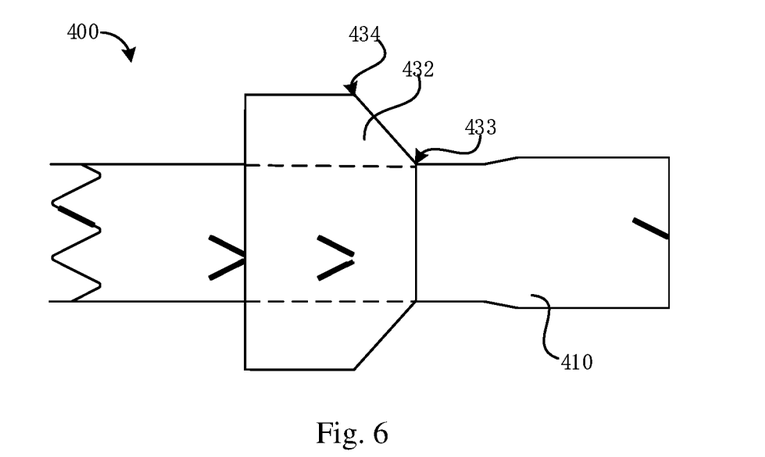
FIG. 6 is schematic diagram showing a structure of a double-layer blood vessel stent in natural state in another embodiment.

Referring to FIG. 6, a structure of a double-layer developing stent 400 in another embodiment is substantially the same as that of the double-layer developing stent 300, therefore, it will not be described in detail herein. A difference lies in that the tapered section 432 of the double-layer developing stent 400 obliquely extends towards the free end 434 from the connecting end 433, and an included angle γ is formed between the connecting line from the connecting end 433 to the free end 434, and the axis of the main body stent 410, 0<γ<90°.

The various features of the above-mentioned embodiments may be combined in any way, and in order to simplify the description, not all possible combinations of the features of the above-mentioned embodiments are described, however, as long as there is no conflict between these features, they should be considered to be within the scope.

The embodiments described above represent only a few embodiments of the present disclosure, the description of which is specific and detailed, but should not be construed to limit the scope. It can be noted that several variations and modifications may be made by those of ordinary skill in the art without departing from the spirit of the present disclosure, which all fall within the scope of the present disclosure.

The invention claimed is:

1. A double-layer blood vessel stent, comprising: a main body stent, a skirt-sided stent and a developing member, the main body stent further comprising a first end and a second end opposite to the first end;
the skirt-sided stent is arranged outside the main body stent and extends towards the first end; the skirt-sided stent comprises a tapered section and a extending section, and the tapered section is provided with a connecting end and a free end opposite to the connecting end, and the connecting end is connected with the main body stent; and the free end is connected with the extending section; the developing member comprises a first developing member and a second developing member; the first developing member is located between the first end and the connecting end, and the second developing member is located between the first developing member and the first end;
the first developing member comprises a first developing portion and a second developing portion, and the first developing portion extends along a first direction, the second developing portion extends along a second direction; the second direction obliquely intersects with the first direction, and the length of the first developing portion and the length of the second developing portion in an axial direction of the main body stent are both not less than 0.5 mm;
a distance between the first developing portion and the second developing portion on a plane perpendicular to the axial direction of the main body stent gradually increases from a position where the distance between the first developing portion and the second developing portion on a plane perpendicular to the axial direction of the main body stent is the minimum distance to an end, away from the connecting end, of the first developing portion or the second developing portion; the minimum distance between the first developing portion and the second developing portion on the plane perpendicular to the axial direction of the main body stent is not greater than 2 mm;
the first developing portion and the second developing portion are flush with the free end at a position where the distance between the first developing portion and the second developing portion on a plane perpendicular to the axial direction of the main body stent is the minimum distance; and one end, away from the first end, of the second developing member is flush with one end, away from the tapered section, of the extending section.

2. The double-layer blood vessel stent according to claim 1, wherein a distance between one end, close to the connecting section, of the first developing portion and one end, close to the connecting section, of the second developing portion, on the plane perpendicular to the axial direction of the main body stent, is the minimum distance.

3. The double-layer blood vessel stent according to claim 1, wherein the second developing member comprises a third developing portion and a fourth developing portion, and the third developing portion extends along a third direction, and the fourth developing portion extends along a fourth direction; the fourth direction obliquely intersects with the third direction; and the length of the third developing portion and the length of the fourth developing portion in the axial direction of the main body stent are both not less than 0.5 mm;
a distance between the third developing portion and the fourth developing portion on a plane perpendicular to the axial direction of the main body stent gradually increases from a position where the distance between the third developing portion and the fourth developing portion on a plane perpendicular to the axial direction of the main body stent is the minimum distance to an end, away from the connecting end, of the third developing portion or the fourth developing portion; the minimum distance between the third developing portion and the fourth developing portion on a plane perpendicular to the axial direction of the main body stent is not greater than 2 mm;
a distance between one end, away from the first end, of the third developing portion and one end, away from the first end, of the fourth developing portion, on the plane perpendicular to the axial direction of the main body stent is the minimum distance.

4. The double-layer blood vessel stent according to claim 3, wherein the main body stent comprises a first bare stent and a main body coating film attached on the first bare stent; and the first developing portion, the second developing portion, the third developing portion, and the fourth developing portion are all disposed on the first bare stent.

5. The double-layer blood vessel stent according to claim 4, wherein the first bare stent comprises a plurality of axially arranged wave rings, and each wave ring comprises a plurality of alternately arranged wave crests and wave troughs, and an adjacent wave crest and wave trough are connected with each other via a wave rod; and the first developing portion and the second developing portion are located on two adjacent wave rods of one of the wave rings, and the third developing portion and the fourth developing portion are located on two adjacent wave rods of another one of the wave rings.

6. The double-layer blood vessel stent according to claim 5, wherein lengths of the first developing portion, the second developing portion, the third developing portion, and the fourth developing portion are all ½ to ⅔ of that of corresponding wave rods.

7. The double-layer blood vessel stent according to claim 5, wherein the first and second developing members are formed by coating, laminating or winding developing materials on the wave rods of the wave rings where the first and second developing members are located.

8. The double-layer blood vessel stent according to claim 3, wherein an included angle formed between a position where a distance between the first and second developing portions on the plane perpendicular to the axial direction of the main body stent is the minimum distance, and the position where a distance between the third and fourth developing portions on the plane perpendicular to the axial direction of the main body stent is the minimum distance, covered in a peripheral direction of the main body stent, is not greater than 15°.

9. The double-layer blood vessel stent according to claim 1, wherein an axial distance from a position where a distance between the first developing portion and the second developing portion on the plane perpendicular to the axial direction of the main body stent is the minimum distance to an end, away from the first end, of the second developing member, ranges from 10 mm to 15 mm.

10. The double-layer blood vessel stent according to claim 1, wherein an axial distance between one end, away from the first end, of the second developing member, and the first end ranges from 10 mm to 15 mm.

11. The double-layer blood vessel stent according to claim 1, wherein distances from each position on the extending section to the longitudinal center axis of the main body stent are equal.

12. The double-layer blood vessel stent according to claim 1, wherein a sum of a length of a contour line of the tapered section and a length of a contour line of the extending section is not greater than the axial distance from the connecting end to the first end of the main body stent.

13. The double-layer blood vessel stent according to claim 1, wherein the developing member further comprises a third developing member and a fourth developing member; and the third developing member is arranged on the first end, and the fourth developing member is arranged on the second end.

14. The double-layer blood vessel stent according to claim 13, wherein the third and fourth developing members are arranged on wave rings with wave rods, the third and fourth developing members are formed by coating, laminating or winding developing materials on the wave rods of the wave rings where the third and fourth developing members are located.

15. The double-layer blood vessel stent according to claim 1, wherein the tapered section of obliquely extends towards the free end from the connecting end, and an included angle $\gamma$ is formed between a connecting line from the connecting end to the free end, and the axis of the main body stent, $0<\gamma<90°$.

* * * * *